United States Patent [19]

Koeneman

[11] Patent Number: 4,584,995
[45] Date of Patent: Apr. 29, 1986

[54] EXTERNAL FIXATION DEVICE

[75] Inventor: James B. Koeneman, Phoenix, Ariz.

[73] Assignee: Orthotic Limited Partnership, Tempe, Ariz.

[21] Appl. No.: 604,047

[22] Filed: Apr. 26, 1984

[51] Int. Cl.[4] .............................................. A61F 5/04
[52] U.S. Cl. ................................. 128/92 A; 128/92 R
[58] Field of Search ................ 128/92 R, 92 A, 84 R, 128/84 B

[56] References Cited

U.S. PATENT DOCUMENTS

| 2,080,802 | 5/1937 | Anderson | 128/92 A |
|---|---|---|---|
| 2,371,519 | 3/1945 | Haynes | 128/92 A |
| 2,398,915 | 4/1946 | Bell | 128/92 A |
| 2,434,431 | 1/1948 | Pincock | 128/92 A |
| 3,547,113 | 12/1970 | Swanson | 128/92 A |
| 3,877,424 | 4/1975 | Murray | 128/92 A |
| 3,977,397 | 8/1976 | Kalnberz et al. | 128/92 A |

FOREIGN PATENT DOCUMENTS

| 2532539 | 6/1976 | Fed. Rep. of Germany | 128/92 A |
|---|---|---|---|
| 2086231 | 5/1982 | United Kingdom | 128/92 A |
| 770487 | 10/1980 | U.S.S.R. | 128/92 A |

Primary Examiner—Robert Peshock
Assistant Examiner—C. W. Shedd
Attorney, Agent, or Firm—Wood, Herron & Evans

[57] ABSTRACT

An external fixation device for the reduction of severely compounded or infected long bone fractures with substantial soft tissue involvement comprises at least two sets of retaining pins, each set including at least one retaining pin adapted to secure the bone portion distally or proximally of the fracture, a frame having a center section disposed between spaced end sections, and a pair of coupling elements mounted to the end sections of the frame each connecting one set of retaining pins to the frame. One of the coupling elements is adapted to move longitudinally, parallel to the longitudinal axis of the frame so as to properly position and secure one set of retaining pins and the bone portion connected thereto. The other coupling element is connected to a second set of retaining pins and is adapted to translate and pivot such pins, and the bone portion attached thereto, about three mutually orthogonal axes independently of the first coupling element. The frame and coupling elements of the fixation device are preassembled to simplify installation of the device during a surgical precedure and to facilitate post-operative distraction or compression of the fracture site.

14 Claims, 6 Drawing Figures

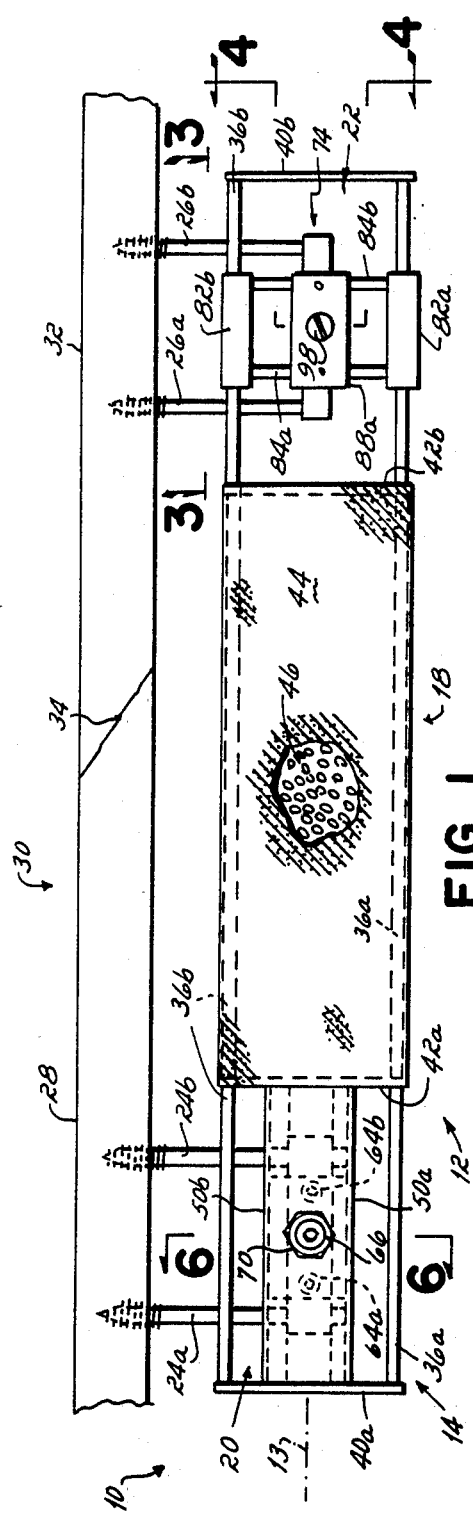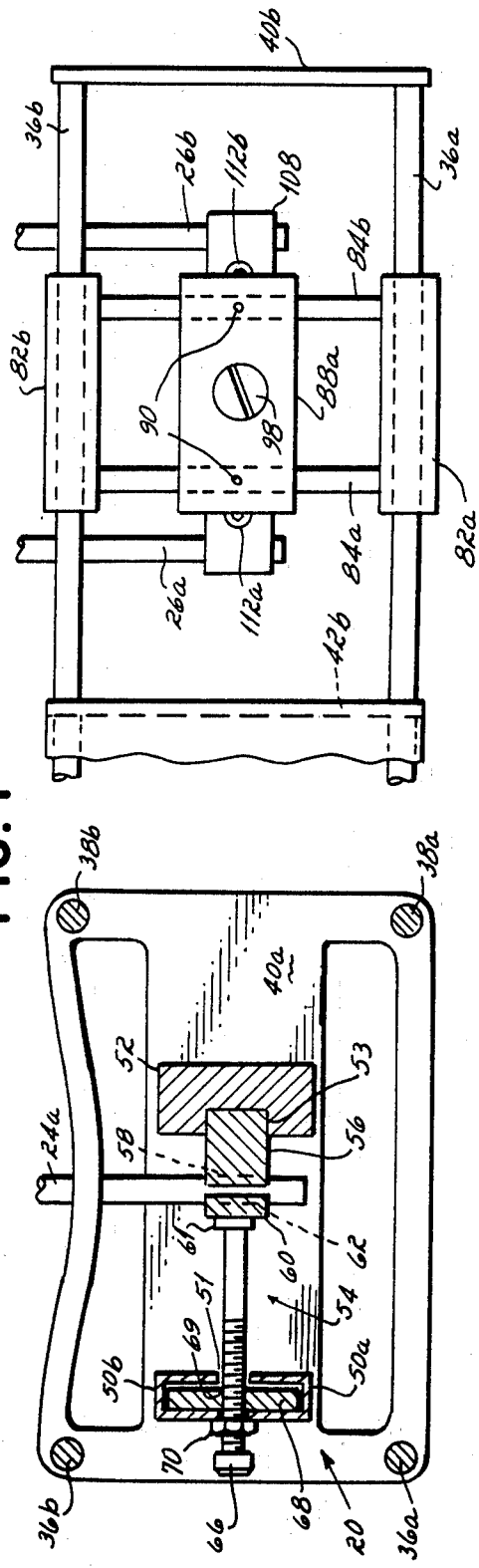

EXTERNAL FIXATION DEVICE

BACKGROUND OF THE INVENTION

This invention relates generally to devices for the treatment of fractures in which soft tissue damage is present, and, more particularly, to a preassembled, unilateral external fixation device operable to reduce a bone fracture and to apply controlled distraction and compression at the fracture site of a bone.

A variety of activities such as high speed travel and the widespread use of heavy machinery in industry have in recent years increased the frequency of severely compounded and infected long bone fractures, such as the femur, tibia, radius and ulna, with accompanying damage to the surrounding soft tissue. In order to properly irrigate the wound and prevent infection of the soft tissue, it is necessary to avoid covering the affected area except with appropriate dressings. Casts may not be used for the treatment of long bone fractures where soft tissue damage is present.

The earliest method of treatment of these cases, which is still used today, involves placing the patient in traction to completely immobilize the affected limb. As is well known, there are many problems attendant to long term confinement of a patient to a bed including necrosis and muscle atrophy. In order to limit the use of traction in the treatment of fractured bones with attendant soft tissue damage, research begun in the 1930's resulted in the development of external skeletal fixation devices. These devices generally comprise a set of retaining pins secured to the bone on each side of the fracture which are adjustably connected to a frame.

An external fixation device commonly used today is the so-called Hoffmann system originally developed in the late 1930's. The Hoffmann fixation system includes two sets of self-drilling and self-tapping transcortical pins each having a centrally located continuous thread. One set of two or three pins enters the soft tissue at one side of the fracture site, passes completely through the distal or proximal portion of the bone and then outwardly through the soft tissue on the opposite side. The same procedure is repeated for the other set of transcortical pins on the opposite side of the fracture. Each transcortical pin is connected at opposite ends to a frame which is adapted to permit translation and pivoting of the pins for properly aligning the distal and proximal bone portions. The frame is adjusted during the surgical procedure to properly align the bone portions, and controlled distraction or compression may be applied post-operatively to maintain the fractured bone portions in engagement and in alignment.

Known external fixation devices incorporate different frame configurations for supporting the transcortical pins such as bilateral, triangular, circular and quadrilateral frames. The above-described Hoffmann device employs a quadrilateral frame. In each of these prior art fixation devices, transcortical pins are used to support the fractured bone portions, which, as described above, extend completely through the soft tissue and bone in the affected limb.

Several problems are encountered with the use of transcortical pins, and with the various frame designs for properly positioning the pins in the distal or proximal bone portions. Assume a patient has a femoral fracture with substantial soft tissue damage at one or more locations along the thigh. The transcortical pins are first inserted into the soft tissue on the distal and proximal side of the fracture. The surgeon can manipulate each transcortical pin around nerves and arteries in the soft tissue until it contacts the femur and begins to enter the cortical bone. At that point, the path of the pin is fixed and no further manipulation is possible. There is a substantial risk of nerve and arterial damage as the pin passes through the femur and then through the soft tissue in a fixed path on the opposite side of the leg. Each of the quadrilateral, circular, triangular and bilateral external fixation devices utilizes transcortical pins.

A second major problem with existing external fixation devices, and particularly the Hoffmann device, is that the frame elements for supporting the transcortical pins are not preassembled but must be assembled by the surgeon during the operation. An assortment of clamping elements and adjustment mechanisms forming the Hoffmann frame are provided to the surgeon in separate pieces and must be fitted together and then clamped to the transcortical pins during the surgical procedure. It has been found that unless the surgeon has great familiarity with the Hoffmann device, or other unassembled frame devices, there may be a reluctance to employ an external fixation device at all.

Another disadvantage of known external fixation devices is the difficulty in adjusting the position of and force exerted by the retaining pins, both during and after an operation. During a surgical procedure and post-operatively, external fixation devices must be capable of adjustment to vary the position of the bone portions and to control distraction and compression at the fracture side. It is often desirable to make relatively minor corrections of the position or force exerted by a set of retaining pins on one side of the fracture. However, in the Hoffmann quadrilateral fixation device, movement of the frame elements to adjust the position of one set of retaining pins in any direction requires adjustment of other frame elements associated with the other set of retaining pins. This feature of the Hoffmann device unduly complicates post-operative adjustment procedures which further reduces the willingness of physicians to employ such devices.

As stated above, one purpose of external fixation devices is to enable patients to move about and reduce the incidents of necrosis and other problems caused by confinement to bed. Many of the frame designs for securing transcortical pins, including the Hoffmann quadrilateral system and circular frames such as shown in U.S. Pats. Nos. 4,365,624 and 4,308,863, are extremely bulky and make it difficult for the patient to walk or otherwise move about. In addition, bulky frames often cover the fracture site and obstruct X-rays. While the retaining pins must be firmly secured to apply the necessary force to the fractured bone portions, it is desirable to make the frame as light as possible without obstructing the fracture site.

SUMMARY OF THE INVENTION

In a broad aspect of this invention, a unilateral external fixation device is provided for treating bone fractures with attendant soft tissue damage which is lightweight, preassembled, and permits universal adjustment of at least one set of retaining pins independently of another set of retaining pins.

More specifically, the external fixation device of this invention comprises at least two sets of retaining pins, each set including at least one retaining pin threaded at one end which is adapted to enter the soft tissue and seat within the fractured bone distally or proximally of the fracture site. A preassembled frame is provided having spaced end sections and a center section disposed therebetween. A longitudinal coupling element is mounted at one of the end sections of the frame which is adapted to clamp one set of retaining pins and move them, and the bone portion secured thereto, longitudinally along an axis substantially parallel to the longitudinal axis of the frame. A universal coupling element is mounted at the other end section of the frame and is adapted to clamp another set of retaining pins which secure the other bone portion on the opposite side of the fracture. The universal coupling element is adapted to translate and pivot about three mutually orthogonal frame axes so as to position the retaining pins and bone portion attached thereto in alignment with the other bone portion. The longitudinal and universal coupling elements together secure the distal and proximal bone portions in proper alignment and apply controlled distraction or compression at the fracture site to promote healing.

In a more specific aspect of this invention, the frame comprises a pair of spaced end plates and a pair of spaced intermediate plates disposed between the end plates. The space between the intermediate plates defines the center section of the frame, and the frame end sections are formed by the space between an intermediate plate and an adjacent end plate at each end of the frame. The end plates and intermediate plates are interconnected by four rods, one fixed at each corner of the plates, which are continuous along the length of the frame. Preferably, the center section includes a body of low density material such as plastic foam disposed between the intermediate plates and bounded by the four rods, which is encased by at least one layer of composite material such as epoxy impregnated glass fibers. The composite material adds to the torsional and bending rigidity of the frame, and the body of foam material prevents buckling of the composite casing and carries much of the shear load. In addition, the composite material and foam body do not block x-rays so that the fracture site is unobstructed by the frame of the invention.

In another specific aspect of this invention, a longitudinal coupling element is disposed at one end section of the frame. A track extends between the end plate and intermediate plate at such end section, which is adapted to receive a clamping element longitudinally movable along the track parallel to the longitudinal axis of the frame. The clamping element is adapted to secure one end of a set of retaining pins, which, together with the bone portion attached thereto, are longitudinally movable with the clamping element.

In a further aspect of this invention, a universal coupling element is disposed at the other end section of the frame. The universal coupling element includes a central rod along which a clamping element is releasably mounted for translation and pivotal motion about the axis of the rod. The clamping element is adapted to secure one end of another set of retaining pins connected to the other bone portion opposite the fracture from the bone portion secured by the longitudinal coupling element. Each end of the central rod is connected to an adjustment assembly, which, in turn, is movably mounted to the rods forming the frame. The adjustment assembly is adapted to permit translation and pivotal motion of the central shaft, and in turn the clamping element, about one axis which is substantially parallel to the longitudinal axis of the frame, and about a second axis which is substantially perpendicular to the longitudinal axis of the frame. The clamping element is therefore adapted to translate and pivot about three mutually orthogonal axes of the frame by operation of the universal coupling element herein, so as to permit manipulation of the bone portion connected thereto for alignment with the other bone portion at the fracture site.

The unilateral external fixation device of this invention provides several advantages over known fixation devices. In conducting a surgical procedure for repairing a fracture of the femur or any other long bone, the retaining pins of this invention can be manipulated within the soft tissue of the affected area distally or proximally of the fracture site so as to avoid damage to nerves, arteries and vessels of the soft tissue. The retaining pins are secured in the bone and protrude from only one side of the affected limb. There is no damage to the soft tissue on the opposite side of the damaged bone as can easily occur when using transcortical pins.

With the retaining pins in place, the frame is then positioned so that the clamping elements of the lateral and universal coupling elements each receive a set of retaining pins. Unlike many prior art fixation devices, the frame of this invention is a preassembled structure and requires no assembly by a surgeon during the operation. The bone portion connected to the longitudinal coupling assembly is properly positioned and then secured in place by tightening the coupling element. The bone portion on the opposite side of the fracture, connected to the universal coupling element, is then manipulated to align with the now fixed bone portion at the fracture site. The universal coupling element is adjustable independently of the longitudinal coupling element so that either the distal or proximal bone portion may be moved without disturbing the position of the other bone portion. Independent adjustment of the bone portions distally and proximally of the fracture site is not permitted in prior art fixation devices. The fixation device of this invention is strong, lightweight, allows a great deal of patient mobility, particularly in leg fractures, and includes a center section which does not obstruct X-rays of the fracture site.

DESCRIPTION OF THE DRAWINGS

The structure, operation and advantages of this invention will become further apparent upon consideration of the following description taken in conjunction with the accompanying drawings, wherein:

FIG. 1 is a plan view of the external fixation device of this invention;

FIG. 2 is a partial plan view of the universal clamping element herein;

FIG. 6 is a side view in partial cross section of the lateral clamping element of the invention.

DETAILED DESCRIPTION OF THE INVENTION

Figure 3:
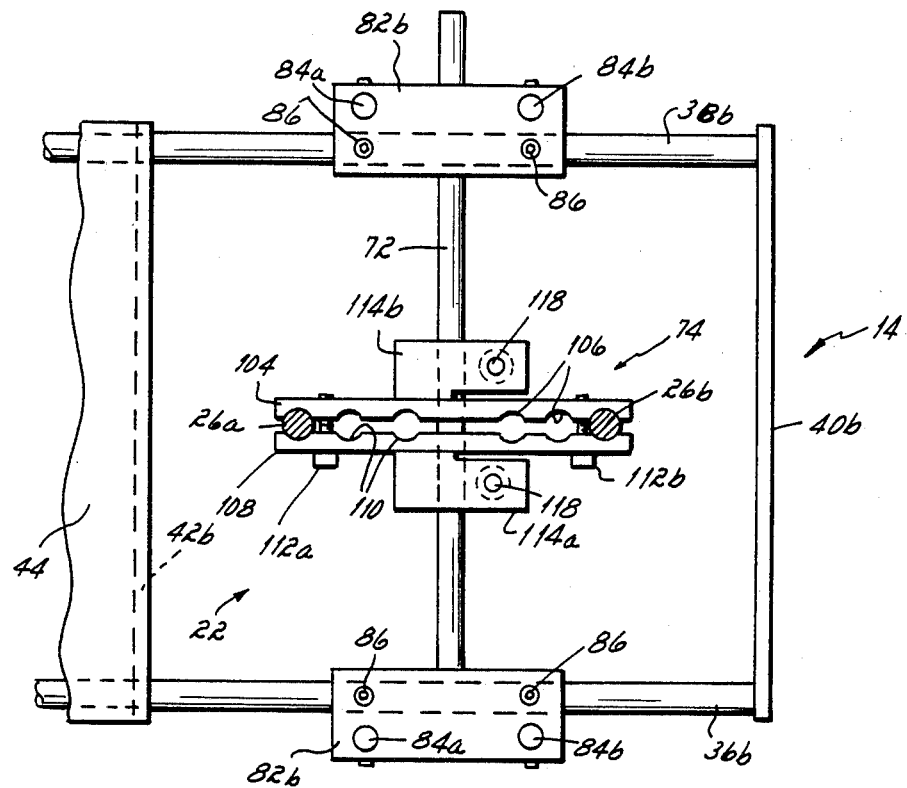
FIG. 3 is a view in partial cross section of the universal clamping element taken generally along line 3—3 of FIG. 1.

Referring now to the drawings, the external fixation device 10 of this invention comprises a frame 12 having spaced end sections 14 and 16 with a center section 18 therebetween, a longitudinally adjustable coupling element 20 disposed at end section 14, a universally adjustable coupling 22 disposed at the other end section 16 and two sets of retaining pins 24a,b and 26a,b secured by the coupling elements 20, 22, respectively. The retaining pins 24a,b extend into the proximal portion 28 of a long bone 30 such as a femur, tibia, radius or ulna, and the second set of retaining pins 26a,b are secured to the distal portion 32 of bone 30 which has a fracture 34 therebetween. The external fixation device 10 is operable to adjust the position of the proximal and distal portions 28,32 of the bone 30 to align and reduce the fracture 34, and to apply controlled compression or distraction to the fracture 34 both during surgery and post-operatively. This allows the bone 34 to heal without covering the surrounding soft tissue (not shown) of the affected limb allowing treatment of such tissue.

The frame 12 is preassembled and includes a pair of spaced, parallel upper rods 36a,b which overlie a pair of spaced, parallel lower rods 38a,b. The rods 36a,b and 38a,b extend the length of frame 12 and are connected at one end to an end plate 40a and at the other end to an end plate 40b. The upper rods 36a,b are fixed by welding or other means to opposite upper corners of the end plates 40a,b and the lower rods 38a,b are similarly attached to opposite bottom corners of the end plates 40a,b. A pair of spaced, intermediate plates 42a,b are mounted at their upper and lower corners to the upper rods 36a,b and lower rods 38a,b, respectively. The intermediate plate 42a is spaced from the end plate 40a to form the end section 14 of frame 12, and intermediate plate 42b is spaced from the end plate 40b to form the opposite end section 16. The center section 18 of frame 12 extends between intermediate plates 42a,b, and includes that portion of the upper rods 36a,b and lower rods 38a,b disposed between the intermediate plates 42a,b.

The frame 12 is subjected to forces in different loading modes including shear, bending, torsion, tension and compression to secure and retain the proximal and distal portions 28, 32 of the bone 30 in position. To enhance the torsional and bending rigidity of frame 12, a casing 44 of composite material is wrapped around the upper rods 36a,b and lower rods 38a,b within the center section 18. Preferably, the composite casing 44 comprises a plurality of individual layers of high tensile strength fiber material, such as graphite, glass or Kevlar ® fiber, which are impregnated with a matrix material such as epoxy. (Kevlar ® is a registered trademark of E. I. DuPont de Nemours Company.) An endless fiber or roving impregnated with epoxy is wrapped around the rods 36a,b and 38a,b along the entire length of center section 18 to form each layer of casing 44. The composite layers forming casing 44 have fibers oriented at various plus or minus angles relative to the longitudinal axis 13 of frame 12, with a plus or minus 45° angle being optimum to increase the stiffness of frame 12 under the application of torque applied along the axis 13. Other individual layers of composite material forming the casing 44 are wrapped about the rods 36a,b and 38a,b parallel (0° angle) to the longitudinal axis 13.

In order to resist buckling of the composite casing 44 in response to bending forces applied to frame 12, and to carry shear load, a solid body 46 of low density material such as polyurethane foam is disposed in the interior of center section 18 between the upper and lower rods 36a,b and the intermediate plates 42a,b. The foam body 46 is lightweight, as is the composite casing 44, and the casing 44 and body 46 do not block X-rays.

The proximal portion 28 of the bone 30 is connected to the frame 12 and held in place by the longitudinally adjustable coupling element 20 and retaining pins 24a,b. Referring to FIGS. 1 and 6, the coupling element 20 includes a track comprising a pair of spaced U-shaped elements 50a,b overlying a lower track plate 52. The space 51 between the channels 50a,b aligns with a groove 53 formed in the lower plate 52, and both the channels 50a,b and lower plate 52 are connected at opposite ends to the end plate 40a and intermediate plate 42a. A clamping element 54 extends between the channels 52a,b and lower plate 52 of the track and is movable longitudinally between the end plate 40a and intermediate plate 42a along an axis parallel to the longitudinal axis 13 of frame 12.

The clamping element 54 comprises a lower plate 56 formed with a number of spaced, semi-circular grooves 58 on its upper surface, and an upper plate 60 overlying the lower plate 56 which is formed with spaced, semi-circular grooves 62 in alignment with the lower plate grooves 58 (similar to the grooves 106, 110 of FIG. 3). The plates 56, 60 are adapted to receive one end of each of the retaining pins 24a,b, which seat between the aligning grooves 58, 62. Screws 64a,b extend between the upper and lower plates 56, 60 and are tightened to move the plates 56, 60 together for securely clamping the retaining pins 24a,b therebetween. In the embodiment of this invention shown in FIGS. 1 and 6, the clamping element 54 is movable and releasably secured along the track as follows. The bottom of lower plate 56 is formed to slide within the groove 53 formed in the track plate 52. A rod 66 extends through the space 51 between U-shaped channels 50a,b and contacts the top surface of upper plate 60 within a collar 61. A guide plate 68, formed with a drilled and tapped bore 69, is threaded onto rod 66 immediately beneath the U-shaped channels 50a,b. The guide plate 68 is formed to slide along the channels 50a,b as the lower plate 56 of clamping element 54 slides with the groove 53 in track plate 52. In order to releasably secure the clamping element 54 in place along track 48, a lock nut 70 is threaded onto rod 66 immediately above the channels 50a,b. The rod 66 is rotated and presses against the upper plate 60 of clamping element 54, which in turn urges the lower plate 56 thereof against the groove 53 in track plate 52. The rod 66 is prevented from rotating in the opposite direction to release pressure against plate 60 by the lock nut 70. Clamping element 54 is released by loosening lock nut 70 and rotating rod 66 in the opposite direction.

Figure 4:
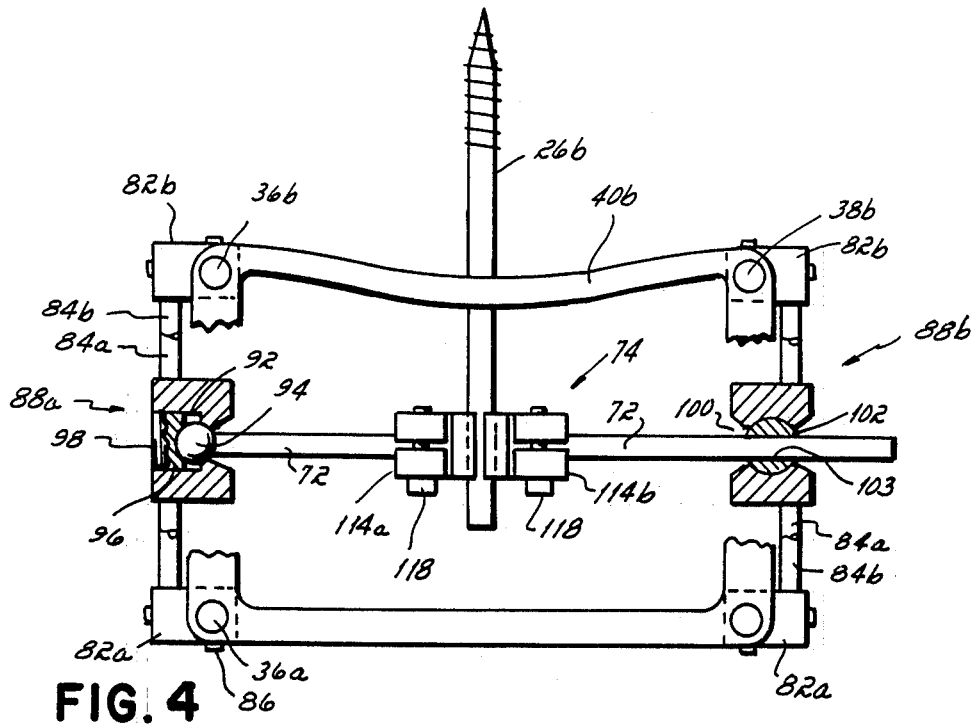
FIG. 4 is a side view in partial cross section of a portion of the universal clamping element shown in FIGS. 2 and 3.
Figure 5:
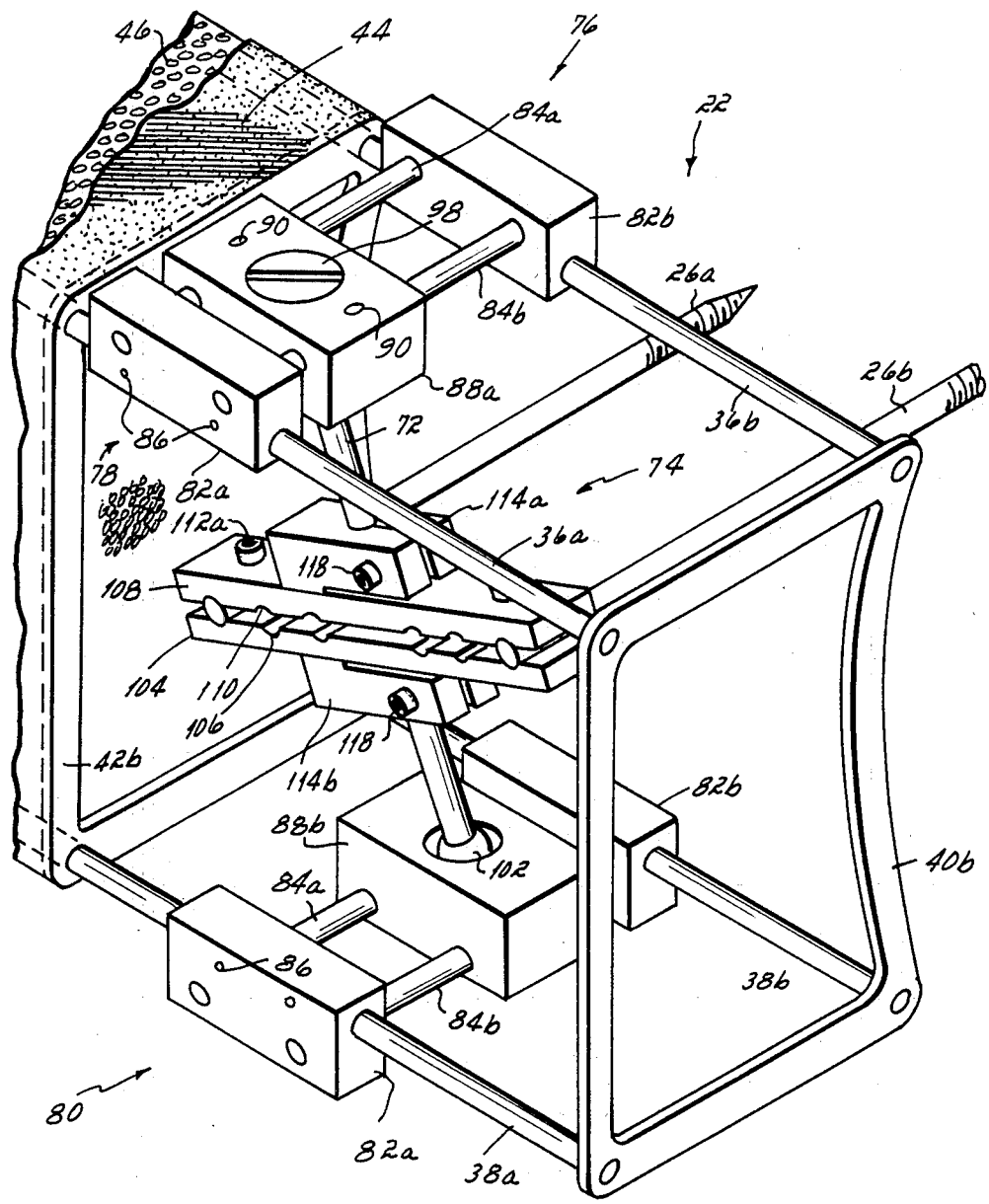
FIG. 5 is an isometric view of the universal external clamping element herein.

Referring to FIGS. 3, 4 and 5, the distal portion 32 of bone 30 is connected to the frame 12 and secured in place by retaining pins 26a,b and the universally adjustable coupling element 22 mounted at the opposite end section 16. As discussed below, the coupling elements 20, 22 cooperate to properly position the distal and proximal portions 28, 32 of the bone 30 to permit healing of fracture 34. The universally adjustable coupling element 22 comprises a central rod 72, a clamping element 74 releasably mounted to the central rod 72, and an adjustment assembly 76. The clamping element 74 is adapted to secure one end of the retaining pins 26a,b, and the adjustment assembly 76 permits universal movement of the rod 72, and in turn clamping element 74, so as to position the retaining pins 26a,b and the distal portion 32 of the bone 30 in any desired location.

The adjustment assembly 76 comprises an upper carriage assembly 78 mounted to the upper rods 36a,b of end section 16, and a substantially similar lower carriage assembly 80 mounted to the lower rods 38a,b at end section 16. For purposes of this discussion, only the upper carriage assembly 78 will be discussed in detail with like reference numerals identifying the same structural elements on the lower carriage assembly 80.

Upper carriage assembly 78 includes a clamp 82a mounted to and slidable along upper rod 36a and a second clamp 82b slidable along the upper rod 36b. A pair of spaced support rods 84a,b extend between the corners of clamps 82a,b, and are mounted thereto by welding or other suitable means. A locking element such as a threaded stud or set screw 86 extends through each end of the clamps 82a,b and is adapted to be advanced into contact with the upper rods 36a,b to releasably lock the clamps 82a,b in a desired position therealong. A center clamp 88a is mounted to the support rods 84a,b between the clamps 82a,b and is slidable therealong. A pair of set screws 90, identical to set screws 86, extend through opposite ends of the center clamp 88a and are adapted to be threaded into engagement with respective support rods 84a,b to secure the center clamp 88a therealong. As shown in FIG. 4, the center clamp 88a is formed with a cavity 92 which is adapted to receive a ball 94 attached at one end of the central rod 72. The ball 94 engages and is pivotal within a socket 96 disposed within the center clamp cavity 92. The socket 96 is held in place within cavity 92 by a threaded cap 98 which engages mating threads formed near the outer edge of cavity 92.

The lower carriage assembly 80 is identical to the upper carriage assembly 78 except for the construction of the center clamp, identified with the reference numeral 88b. The center clamp 88b of lower carriage assembly 80 is formed with a through bore 100 in which a bearing 102 having an opening 103 is pivotally mounted. The end of central rod 72 opposite ball 94 extends through the bore 100 and into the opening 103 in bearing 102. As discussed below, the center clamps 88a, 88b of the carriage assemblies 78, 80 permit universal pivotal motion of the central rod 72 and the clamping element 74 mounted thereto.

Referring now to FIGS. 3 and 5, the clamping element 74 of the universally adjustable coupling element 22 is shown. Clamping element 74 includes a lower plate 104 formed with spaced, semicircular grooves 106 on its upper surface, and a bore adapted to receive the central shaft 72 so that the lower plate 104 is movable therealong. Overlying the lower plate 104 is an upper plate 108 having semi-circular grooves 110 aligning with grooves 106, which is also formed with a bore to receive the central shaft 72 for movement of the upper plate 108 therealong. The plates 104, 108 are connected by a pair of screws 112a,b which are adapted to tighten them together to clamp one end of the retaining pins 26a,b within the aligning grooves 106, 110 formed in plates 104, 108.

The clamping element is releasably mounted in a fixed position along central rod 72 by a pair of U-shaped clamps 114a,b, mounted to the upper and lower plates 108, 104, respectively. The clamps 114a,b are adapted to receive the central shaft 72 within the curved portion of the U shape so as to be movable therealong with plates 104, 108 (see also FIG. 4). A screw 118 extends between the spaced legs of each U-shaped clamp 114a,b, which is adapted to be tightened so as to urge the legs together and releasably secure the U-shaped clamps 114a,b in a fixed position along the central rod 72.

The external fixation device 10 of this invention provides several advantages in construction and operation over known fixation devices, and these advantages may be best appreciated by an explanation of the use of external fixation device 10 in securing the proximal and distal portions 28, 32 of a fractured bone 30. Initially, the fracture site 34 of the bone 30 is located and a template (not shown) is used by the surgeon to approximate the appropriate spacing between the retaining pins 24a,b along the proximal bone portion 28 and retaining pins 26a,b along the distal bone portion 32. As shown in the drawings, the retaining pins 24, 26 are provided with a pointed end which is self drilling and self tapping, and are threaded from the pointed end at least partially along the shaft. Retaining pins 24, 26 are not transcortical pins; instead, they are half-pins inserted into the soft tissue of a limb on one side of the bone 30 and then at least partially into the bone 30 but not through the other side. During insertion, the surgeon can manipulate the pins 24, 26 to avoid damaging nerves, veins, and arteries within the soft tissue. Once in place, the opposite ends of the retaining pins 24, 26 extend outwardly from one side of the bone 30.

An important aspect of the external fixation device 10 of this invention is that the frame 12 requires no assembly during the surgical procedure. This is in contrast to many known fixation devices which require complete assembly of a number of different structural pieces during the operation. The assembled frame 12 herein enables the surgeon to simply move it into place so that the outwardly extending ends of the retaining pins 24a,b are received by the laterally adjustable coupling element 20 and the ends of retaining pins 26a,b are received by the universally adjustable coupling element 22.

It has been found desirable to secure either the proximal or distal portion 28, 32 of bone 30 in a fixed, properly aligned position and then manipulate the other bone portion separately to reduce the fracture 34. For purposes of discussion, it is assumed herein that the proximal portion 28 is initially fixed in place. If the proximal portion 28 of bone 30 is dislocated from its normal position, the surgeon can position it by hand through the soft tissue or by manipulating the outwardly-extending end of the retaining pins 24a,b before the frame 12 is moved into place. Once the proximal bone portion 28 is generally located, the frame 12 is positioned so that the retaining pins 24a,b are received within the clamping element 54 of coupling element 20. The screws 64a,b are then tightened to secure the retaining pins 24a,b between the clamping plates 56, 60. With the retaining pins 24a,b clamped to the coupling element 20, further movement of the proximal portion 28 of bone 30 is restricted to translation parallel to the longitudinal axis 13 of frame 12. Such adjustment is accomplished by moving the clamping element 64 along the track formed by U-shaped channels 50a,b and plate 52, and then locking it in a desired position by tightening shaft 66 as described above.

With the proximal portion 28 of bone 30 fixed in place, the distal portion 32 may be independently manipulated by the surgeon using the universally adjustable coupling element 22. The retaining pins 26a,b connected to the distal bone portion 32 are first clamped to the clamping element 74 of coupling element 22. The clamping element 74, and in turn the retaining pins 26a,b and distal portion 32, are then universally movable by operation of coupling element 22.

Referring to FIGS. 1 and 5, the movement of the clamping element 74, and in turn the distal bone portion 32 provided by coupling element 22, consists of both translation and pivotal motion about one or more of three mutually orthogonal axes located at the frame 12. For purposes of discussion, it is assumed that one axis is parallel to the longitudinal axis 13 of frame 12, a second axis is coincident with the longitudinal axis of the central rod 72 and the third axis is transverse to the central rod 72 and longitudinal axis 13.

Translation of clamping element 74 and distal bone portion 32 is permitted with a minimum of adjustment to coupling element 22. The clamping element 74 is movable along the axis of central rod 72 by releasing the U-shaped clamps 114a,b. Movement of the clamping element 74 along an axis parallel to the longitudinal axis 13 of frame 12 is accomplished by loosening the screws 86 securing the clamps 82a,b of both the upper and lower carriage assemblies 78 and 80, and then translating the carriage assemblies 78, 80 along the upper rods 36a,b and lower rods 38a,b, respectively, of the frame 12. The center clamps 88a,b, to which the central rod 72 and clamping element 74 are connected, move as a unit with carriage assemblies 78, 80. Translation of the clamping element 74 along the axis transverse to the longitudinal axis 13, that is, toward and away from the upper and lower rods 36, 38 of the frame 12, is permitted by releasing the screws 90 holding center clamps 88a,b in place along support rods 84a,b. Once released, the center clamps 88a,b are free to slide along the support rods 84a,b and may be clamped in place at any desired location by tightening screws 90.

The universally adjustable coupling element 22 also permits pivotal motion about each of the three frame axes described above. Referring again to FIG. 5, the clamping element 74 is pivotal about the axis of central rod 72 by releasing the U-shaped clamps 114a,b. Pivotal movement about an axis parallel to the longitudinal axis 13 of frame 12 is permitted by releasing the screws 90 securing the center clamps 88a,b to the support rods 84a,b. Movement of the upper center clamp 88 toward upper rod 36b is accompanied by movement of the lower center clamp 88b toward the lower rod 38a. At the same time, each end of the central rod 72 pivots about its bearing connections to the center clamps 88a,b causing the distal bone portion 32 to tip downwardly. The distal bone portion 32 pivots upwardly about the axis parallel to the longitudinal axis 13, as specifically shown in FIG. 5, by reversing the directions of motion of the center clamps 88a,b so that center clamp 88a moves toward the upper rod 36a and center clamp 88b moves toward lower rod 38b. The distal bone portion 32 may be pivoted about the axis transverse to the longitudinal axis by movement of the upper and lower carriage assemblies 78, 80 in the opposite direction along the upper rods 36a,b and lower rods 38a,b, respectively. For example, movment of the upper carriage assembly 78 toward the intermediate plate 42b, as specifically illustrated in FIG. 5, causes the lower carriage assembly 80 to move in the opposite direction toward end plate 40b so that the end of distal bone portion 32 adjacent fracture 34 tilts downwardly. The reverse pivotal or tilting movement of distal bone portion 32 is provided by movement of carriage assemblies 78, 80 in opposite directions.

It should be understood that both pivotal movment and translation of the distal bone portion 32 may be accomplished at the same time by loosening selected clamping mechanisms as described above. In fact, release of the clamping means to prevent translation of the distal bone portion 32 along any one axis also allows pivotal motion thereof about the same axis. It is contemplated that during the initial manipulation of distal bone portion 32, the clamping mechanisms of coupling element 22 would be loosened to permit translation and pivotal motion in all directions. Once the distal bone portion 32 is properly positioned along any one axis, the appropriate clamping mechanism is then tightened to lock the coupling element 22 along such axis. Further independent motion of the distal bone portion 32 along the other two axes is permitted and separately locked in the desired position. In this manner, the surgeon can carefully control positioning of the distal bone portion 32 about each of the three axes independently, either during a surgical procedure or post-operatively, to facilitate adjustment when necessary.

The fixation device 10 has been described as including a longitudinally adjustable coupling element 20 disposed at one end 14 of the frame 12 and a universally adjustable coupling element 22 at the opposite end 16 of the frame 12. It is comtemplated that most bone fractures can be satisfactorily treated with such an arrangement of coupling elements 20, 22. However, in some instances it may be preferred to provide device 10 with universally adjustable coupling elements 22 at both ends 14, 16 of frame 12 to obtain ever greater adjustment of the position of bone portions 28, 32. Alternatively, two longitudinal coupling elements 20 may be disposed at either end 14, 16 of frame 12 where only longitudinal adjustment of bone portions 28, 32 is required. The fixation device 10 is therefore operable to provide a wide range of adjustment capability for a given fracture.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teaching of the invention without departing from the essential scope thereof. Therefore, it is intended that the invention not be limited to the particular embodiment disclosed as the best mode contemplated for carrying out the invention, but that the invention will include all embodiments falling within the scope of the appended claims.

Wherefore I claim:

1. An external fixation device for positioning and immobilizing the distal portion and proximal portion of a fractured bone to reduce the fracture, comprising:
   a frame having opposed ends and a center section therebetween, said center section including a body of low density material encased with at least one layer of composite reinforcement material;
   a first coupling element mounted to one end of said frame, said first coupling element being adapted to clamp retaining pins inserted into one of the proximal and distal portions of the fractured bone;
   a second coupling element mounted to the other end of said frame, said second coupling element being adapted to clamp retaining pins inserted into the other of the proximal and distal portions of the fractured bone;
   said first and second coupling elements being movable with respect to said frame independently of one another to align the proximal and distal portions of the fractured bone for reduction of the fracture.

2. The external fixation device of claim 1 in which said first coupling element comprises:
   a track mounted at one end of said frame, said track including a pair of U-shaped channels spaced from and overlying a lower plate formed with a groove; and
   clamping means for clamping retaining pins inserted into the proximal portion of the fractured bone, said clamping means being movable longitudinally along said pair of U-shaped channels and said lower plate.

3. The external fixation device of claims 2 in which said clamping means comprises:
   a lower plate formed with space grooves;
   an upper plate overlying said lower plate, said upper plate being formed with spaced grooves disposed in alignment with said spaced grooves in said lower plate;
   means extending between said plates for moving said plates together, the retaining pins inserted into the proximal portion of the fractured bone being received within said grooves of said upper and lower plates and being clamped therein by said means for moving said plates together;
   a shaft extending from said upper plate through said space between said U-shaped channels, said shaft being threaded along a portion thereof between said U-shaped channels;
   a plate having a threaded bore, said plate being threaded onto said shaft; and
   a lock nut threaded onto said shaft and spaced from said plate, said U-shaped channels being disposed between said plate and said lock nut.

4. The external fixation device of claim 1 in which said second coupling element comprises:
   a central rod;
   clamping means for clamping one end of retaining pins inserted into the distal portion of the fractured bone, said clamping means being releasably mounted to said central rod, said clamping means being movable along the axis of said central rod and pivotal about said axis;
   adjustment means connected at opposite ends of said central rod for positioning said clamping means and in turn the retaining pins inserted into the distal portion of the fractured bone, said adjustment means being adapted to translate and pivot said clamping means along axes parallel to the longitudinal axis of said frame and perpendicular to said longitudinal axis.

5. An external fixation device as in claim 4 in which said clamping means comprises:
   a lower plate formed with spaced grooves;
   an upper plate overlying said lower plate, said upper plate being formed with spaced grooves disposed in alignment with said spaced grooves in said lower plate;
   means extending between said upper and lower plates for moving said plates together, the retaining pins inserted into the distal portion of the fractured bone being received within said grooves of said upper and lower plates and being clamped therein by said means for moving said plates together.

6. The external fixation device of claim 4 in which said adjustment means comprises;
   an upper carriage assembly including a pair of spaced clamps each movable along an axis substantially parallel to said longitudinal axis of said frame, said clamps being connected together for unitary movement, and a pivot element movable between said clamps along an axis substantially perpendicular to said longitudinal axis, said pivot element including means for pivotally mounting one end of said central shaft; and
   a lower carriage assembly including a pair of spaced clamps each movable along an axis substantially parallel to said longitudinal axis of said frame, said clamps being connected together for unitary movement, and a pivot element movable between said clamps along an axis substantially perpendicular to said longitudinal axis, said pivot element including means for pivotally mounting one end of said central rod.

7. The external fixation device of claim 6 in which said central rod is formed with a ball at one end, said upper carriage pivot element having means for pivotally mounting said ball at the end of said central rod comprising a cavity formed in said upper carriage pivot element and a socket mounted within said cavity, said socket being adapted to engage said ball and permit pivotal motion of said central rod.

8. The external fixation device of claim 6 in which said lower carriage pivot element includes a bearing having a central opening adapted to receive one end of said central rod, said bearing being adapted to pivot within said lower carriage pivot element and thereby permit pivotal motion of said one end of said central rod.

9. The external fixation device of claim 1 in which said center section includes a body of low density material, said body being encased with at least one layer of composite material comprising an endless section of high tensile strength material impregnated with a matrix material.

10. The external fixation device of claim 9 in which said body is formed of plastic foam material.

11. The external fixation device of claim 9 in which said composite material is chosen from the group consisting of graphite fibers, glass fibers and Kevlar fibers.

12. The external fixation device of claim 9 in which said matrix material is epoxy.

13. The external fixation device of claim 9 in which said at least one layer of composite material comprises a roving of high tensile strength material wrapped about said body in layers at various angles relative to the longitudinal axis of said frame, at least one of said layers of said roving of high tensile strength material being layed parallel to the longitudinal axis of said frame.

14. The external fixation device of claim 13 in which said roving of high tensile strength material is wrapped at an angle of ±45° relative to the longitudinal axis of said frame.

* * * * *